United States Patent
Li et al.

(10) Patent No.: US 11,039,757 B2
(45) Date of Patent: Jun. 22, 2021

(54) METHOD AND SYSTEM FOR CARDIAC MOTION CORRECTED MR EXAM USING DEFORMABLE REGISTRATION

(71) Applicant: Cedars-Sinai Medical Center, Los Angeles, CA (US)

(72) Inventors: Debiao Li, South Pasadena, CA (US); Jianing Pang, Chicago, IL (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 914 days.

(21) Appl. No.: 15/359,239

(22) Filed: Nov. 22, 2016

(65) Prior Publication Data
US 2018/0140216 A1 May 24, 2018

(51) Int. Cl.
| | | |
|---|---|---|
| *A61B 5/00* | (2006.01) | |
| *A61B 5/02* | (2006.01) | |
| *A61B 5/055* | (2006.01) | |
| *G01R 33/565* | (2006.01) | |
| *G01R 33/48* | (2006.01) | |
| *G01R 33/563* | (2006.01) | |
| *G01R 33/483* | (2006.01) | |
| *G01R 33/567* | (2006.01) | |

(52) U.S. Cl.
CPC .............. *A61B 5/055* (2013.01); *A61B 5/02* (2013.01); *A61B 5/7207* (2013.01); *G01R 33/56509* (2013.01); *G01R 33/4826* (2013.01); *G01R 33/4838* (2013.01); *G01R 33/5676* (2013.01); *G01R 33/56325* (2013.01)

(58) Field of Classification Search
CPC ........ G01R 33/56509; G01R 33/56325; G01R 33/5676; G01R 33/20–64; A61B 5/7207; A61B 5/055–5/0555
See application file for complete search history.

(56) References Cited

U.S. PATENT DOCUMENTS

2006/0074292 A1* 4/2006 Thomson ............... A61B 6/032
600/411
2014/0079305 A1* 3/2014 Akcakaya ............. G06T 7/0012
382/131

OTHER PUBLICATIONS

Pruessmann KP, Weiger M, Boernert P, Boesiger P. A gridding approach for sensitivity encoding with arbitrary trajectories. In: Proceedings of the 8th Annual Meeting of ISMRM, Denver, p. 276. (Year: 2000).*
Han, F., Ouyang, C., Zhou, Z. et al. "Image-based 3D non-rigid respiratory motion correction for free-breathing thoracic MR angiography". J Cardiovasc Magn Reson 18, p. 15 (Year: 2016).*

(Continued)

*Primary Examiner* — Bill Thomson
*Assistant Examiner* — Amal Aly Farag
(74) *Attorney, Agent, or Firm* — Nixon Peabody LLP

(57) ABSTRACT

In various embodiments, the present invention teaches methods and related systems for imaging the coronary arteries in high spatiotemporal resolution for the assessment of coronary stenosis. In some embodiments, the method teaches the use of a 3D radial k-space trajectory, continuous acquisition, retrospective cardiac and respiratory self-gating, and non-rigid cardiac and respiratory motion correction to reconstruct any arbitrary cardiac phase with minimal motion artifacts and high image quality.

19 Claims, 7 Drawing Sheets

(56) References Cited

OTHER PUBLICATIONS

Avants, B.B. et al., "Symmetric diffeomorphic image registration with cross-correlation: Evaluating automated labeling of elderly and neurodegenerative brain," ScienceDirect, Medical Image Anaylsis 12 (2008) 26-41 (16 pages).

Balu, N. et al., "Cartoid Plaque Assessment Using Fast 3D Isotropic Resolution Black-Blood MRI," Magnetic Resonance in Medicine 65:627-637 (2011) (11 pages).

Batchelor, P.G. et al., "Matrix Description of General Motion Correction Applied to Multishot Images," Magnetic Resonance in Medicine 54:1273-1280 (2005) (8 pages).

Boussel, L. et al., "Altherosclerotic Plaque Progression in Cartoid Arteries: Monitoring with High-Spatial-Resolution MR Imaging—Multicenter Trial," Radiology: vol. 252: No. 3—Sep. 2009, radiology. rsnajnls.org (8 pages).

Chan, R. et al., "Temporal Stability of Adaptive 3D Radial MRI Using Multidimensional Golden Means," Magnetic Resonance in Medicine 61:354-363 (2009) (10 pages).

Chandarana, H. et al., "Free-Breathing Radial 3D Fat-Suppressed T1-Weighted Gradient Echo Sequence," A Viable Alternative for Contrast-Enhanced Liver Imaging in Patients Unable to Suspend Respiration, Investigative Radiology, vol. 46, No. 10, Oct. 2011 (6 pages).

Chung, Y. et al., "2137 T1-weighted 3D dark blood TSE for carotid artery disease imaging—preliminary experience," Journal of Cardiovascular Magnetic Resonance, Oct. 22, 2008, 10(Suppl 1):A406 (3 pages).

Coppo, S. et al., "Free-Running 4D Whole-Heart Self-Navigated Golden Angle MRI: Initial Results," Magnetic Resonance in Medicine 74:1306-1316 (2015) (11 pages).

Crowe, L. et al., "Volume-Selective 3D Turbo Spin Echo Imaging for Vascular Wall Imaging and Distensibility Measurement," Journal of Magnetic Resonance Imaging 17:572-580 (2003) (9 pages).

Deng, Z. et al., "Four-dimensional MRI Using Three-Dimensional Radial Sampling with Respiratory Self-Gating to Characterize Temporal Phase-Resolved Respiratory Motion in the Abdomen," Magnetic Resonance in Medicine, May 2015 (13 pages).

Fan, Z. et al.. "3D Noncontrast MR Angiography of the Distal Lower Extremities Using Flow-Sensitive Dephasing (FSD)—Prepared Balanced SSFP," Magnetic Resonance in Medicine 62:1523-1532 (2009) (10 pages).

Fan, Z. et al., "Carotid Arterial Wall MRI at 3T Using 3D Variable-Flip-Angle Turbo Spin-Echo (TSE) with Flow-Sensitive Dephasing (FSD)," Journal of Magnetic Resonance Imaging 31:645-654 (2010) (10 pages).

Fan, Z. et al., "Multi-Contrast Astherosclerosis Characterization (MATCH) of Carotid Plaque with a Single 5-min scan: Technical Development and Clinical Feasibility," Journal of Cardiovasular Magnetic Resonance 2014, 16:53 (12 pages).

Hardy, C. et al., "Coronary Angiography by Real-Time MRI With Adaptive Averaging," Magnetic Resonance in Medicine 44:940-946 (2000) (7 pages).

Hernandez, M. et al., "Color Fusion of Magnetic Resonance Images Improves Intracranial Volume Measurement in Studies of Aging," Open Journal of Radiology, 2012, 2, 1-9 (9 pages).

Huang, T. et al., "Automatic calibration of trigger delay time for cardiac MRI," NMR in Biomedicine, Published online in Wiley Online Library: Jan. 29, 2014 (8 pages).

Jahnke, C. et al., "A new approach for rapid assessment of the cardiac rest period for coronary MRA," Journal of Cardiovascular Magnetic Resonance (2005) 7, 395-399 (5 pages).

Kelly, J. et al., "Magnetic resonance direct thrombus imaging: a novel technique for imaging venous thromboemboli," Thromb Haemost 2003; 89: 773-82 (10 pages).

Kim, D. et al., "Accelerated Phase-Contrast Cine MRI Using k-t SPARSE-SENSE," Magnetic Resonance in Medicine 67:1054-1064 (2012) (11 pages).

Koktzoglou, I. et al., "Diffusion-Prepared Segmented Steady-State Free Precession: Application to 3D Black-Blood Cardiovascular Magnetic Resonance of the Thoracic Aorta and Carotid Artery Walls," Journal of Cardiovascular Magnetic Resonance (2007) 9, 33-42 (10 pages).

Leach, J. et al., "imaging of Cerebral Venous Thrombosis: Current Techniques, Spectrum of Findings, and Diagnostic Pitfalls," Clinical Applications of Vascular imaging, RadioGraphics 2006; 26:S19-S43 (24 pages).

Li, L. et al., "DANTE-Prepared Pulse Trains: A Novel Approach to Motion-Sensitized and Motion-Suppressed Quantitative Magnetic Resonance Imaging," Magnetic Resonance in Medicine 68:1423-1438 (2012) (16 pages).

Li, D. et al., "Coronary Arteries: Magnetization-prepared Contrast-enhanced Three-dimensional Volume-targeted Breath-hold MR Angiography," Radiology 2001; 219:270-277 (8 pages).

Lingala, S. et al., "Deformation corrected compressed sensing (DC-CS): a novel framework for accelerated dynamic MRI," arXiv:1405.7718v2 [cs.CV] Sep. 2, 2014 (14 pages).

Mihai, G. et al., "T1-Weighted-SPACE Dark Blood Whole Body Magnetic Resonance Angiography (DB-WBMRA): Initial Experience," Journal of Magnetic Resonance Imaging 31:502-509 (2010) (8 pages).

Mugler, J. III, "Optimized Three-Dimensional Fast-Spin-Echo MRI," Journal of Magnetic Resonance Imaging 39:745-767 (2014) (23 pages).

Pang, J. et al., "Whole-Heart Coronary MRA with 100% Respiratory Gating Efficiency: Self-Navigated Three-Dimensional Retrospective Image-Based Motion Correction (TRIM)," Magnetic Resonance in Medicine 71:67-74 (2014) (8 pages).

Pang, J. et al., "ECG and Navigator-Free Four-Dimensional Whole-Heart Coronary MRA for simultaneous Visualization of Cardiac Anatomy and Function," Magnetic Resonance in Medicine 72:1208-1217 (2014) (10 pages).

Park, J. et al., "Optimized T1-Weighted Contrast for Single-Slab 3D Turbo Spin-Echo Imaging With Long Echo Trains: Application to Whole-Brain Imaging," Magnetic Resonance in Medicine 58:982-992 (2007) (11 pages).

Piccini, D. et al., "Is There an Optimal Respiratory Reference Position for Self-Navigated Whole-Heart Coronary MR Angiography?," 2015 Wiley Periodicals, Inc. (8 pages).

Qiao, Y. et al., "Intracranial Arterial Wall Imaging Using Three-Dimensional High Isotropic Resolution Black Blood MRI at 3.0 Tesla," Journal of Magnetic Resonance Imaging 34:22-30 (2011) (9 pages).

Rasche, V. et al., "Automatic extraction of the low-motion phases of the heart," Proc. Intl. Soc. Mag. Reson. Med. 15 (2007) (1 page).

Royuela-Del-Val, J. et al., "Nonrigid Groupwise Registration for Motion Estimation and Compensation in Compressed Sensing Reconstruction of Breath-Hold Cardiac Cine MRI," Magnetic Resonance in Medicine 75:1525-1536 (2016) (12 pages).

Saam, T. et al., "Carotid Plaque Composition Differs Between Ethno-Racial Groups," An MRI Pilot Study Comparing Mainland Chinese and American Caucasian Patients, Arterioscler Thromb Vasc Biol. Mar. 2005 (6 pages).

Saposnik, G. et al., "Diagnosis and Management of Cerebral Venous Thrombosis," A Statement for Healthcare Professionals From the American Heart Association/American Stroke Association, Stroke 2011;42:1158-1192 (35 pages).

Schmidt, J. et al., "Nonrigid Retrospective Respiratory Motion Correction in Whole-Heart Coronary MRA," Magnetic Resonance in Medicine 66:1541-1549 (2011) (9 pages).

Song, H. et al., "Multislice Double Inversion Pulse Sequence for Efficient Black-Blood MRI," Magnetic Resonance in Medicine 47:616-620 (2002) (5 pages).

Stehning, C. et al., "Fast Isotropic Volumetric Coronary MR Angiography Using Free-Breathing 3D Radial Balanced FFE Acquisition," Magnetic Resonance in Medicine 52:197-203 (2004) (7 pages).

Stehning, C. et al., "Free Breathing 3D Balanced FFE Coronary Magnetic Resonance Angiography with Prolonged Cardiac Acquisition Windows and Intra-RR Motion Correction," Magnetic Resonance in Medicine 53:719-723 (2005) (5 pages).

(56) References Cited

OTHER PUBLICATIONS

Takano, K. et al., "Characterization of carotoid atherosclerosis with black-blood carotid plague imaging using variable flip-angle 3D turbo spin-echo: Comparison with 2D turbo spin-echo sequences,"European Journal of Radiology 81 (2012) e304-e309 (6 pages).

Takano, K. et al., "MRI of intracranial vertebral artery dissection: evaluation of intramural haematoma using a black blood, variable-flip-angle 3D turbo spin-echo sequence," Neuroradiology (2013) 55:845-851 (8 pages).

Tustison, N. et al., "Explicit B-spline regularization in diffeomorphic image registration," Frontiers in Neuroinformatics, Methods Article, Dec. 23, 2013, vol. 7, Article 39 (13 pages).

Underhill, H. et al., "MRI of carotid atherosclerosis: clinical implications and future directions," Molecular Imaging, Nature Reviews, Cardiology, vol. 7, Mar. 2010 (9 pages).

Usman, M. et al., "Motion Corrected Compressed Sensing for Free-Breathing Dynamic Cardiac MRI," Magnetic Resonance in Medicine 70:504-516 (2013) (13 pages).

Ustun, A. et al., "Automated Identification of Minimal Myocardial Motion for Improved Image Quality on MR Angiography at 3 T," Cardiac Imaging, Technical Innovation, AJR: 188, Mar. 2007 (8 pages).

Winter, P. et al., "Improved Molecular Imaging Contrast Agent for Detection of Human Thrombus," Magnetic Resonance in Medicine 50:411-416 (2003) (6 pages).

\* cited by examiner

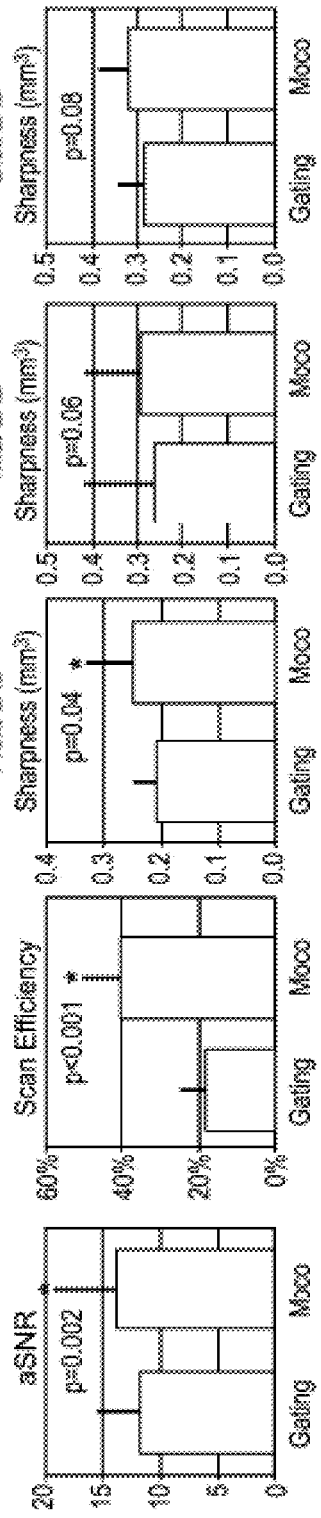
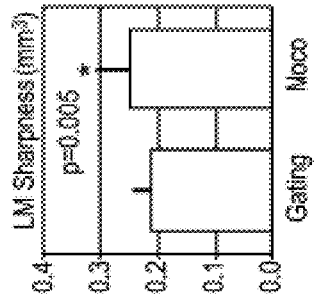
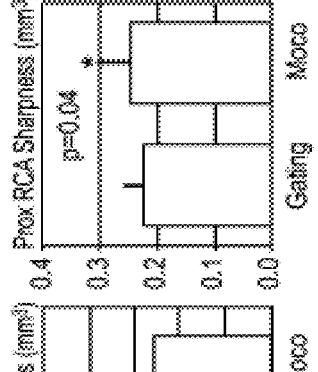
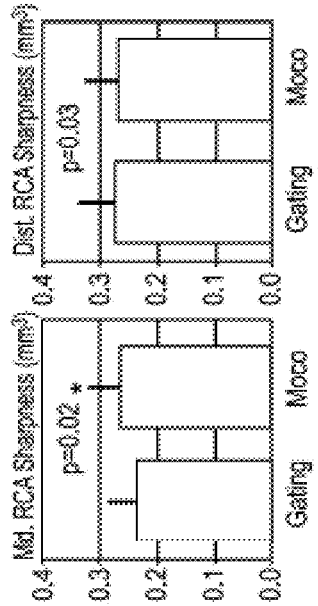
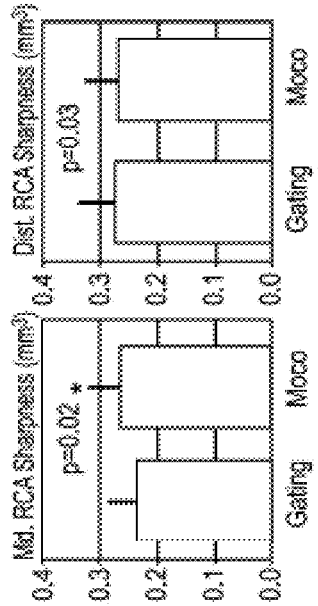

METHOD AND SYSTEM FOR CARDIAC MOTION CORRECTED MR EXAM USING DEFORMABLE REGISTRATION

FIELD OF THE INVENTION

The present invention generally relates to imaging methods, and especially magnetic resonance imaging (MRI) methods.

BACKGROUND

The following description includes information that may be useful in understanding the present invention. It is not an admission that any of the information provided herein is prior art or relevant to the presently claimed invention.

Coronary magnetic resonance angiography (MRA) has shown promise in detecting significant coronary stenosis non-invasively, which is of great clinical importance in the management of coronary artery disease. Favorable sensitivity and specificity values have been shown by studies conducted at academic centers. However, residual cardiac respiratory motion artifacts remain the major challenge for coronary MRA, and lead to considerable diagnostic inaccuracy and scan failures. The conventional motion suppression strategies bear several limitations including (i) vulnerability to motion pattern variations, (ii) prolonged and unpredictable scan time, (iii) operator dependency, and (iv) complex scan workflow. Furthermore, clinically available methods typically suffer from non-isotropic spatial resolution, specifically poor resolution along the superior-inferior direction. Due to above-mentioned technical demands, there are relatively few imaging centers that offer such exams or perform them with significant volume. Addressing these issues would represent a breakthrough in the potential widespread dissemination of this important imaging technique.

There is a need in the art for improved systems and methods for coronary MRA.

SUMMARY

The various embodiments of the present invention generally relates to imaging methods, and especially magnetic resonance imaging (MRI) methods. In a first embodiment, there is provided a method for performing magnetic resonance imaging (MRI) on a subject. The method includes (a) utilizing an MRI scanner to apply a pulse sequence to a region of interest (ROI) comprising one or more coronary blood vessels within the subject, (b) acquiring raw imaging data from the ROI continuously, and (c) reconstructing a four dimensional (4D) image of one or more portions of one or more of the coronary blood vessels within the ROI from said raw imaging data.

In the method of the first embodiment, the pulse sequence can include an ungated, spoiled gradient echo acquisition with golden-angle radial trajectory. Further, the pulse sequence can also include water-selective excitation pulses. Also, the excitation pulses can be slab-selective for suppressing outer volume signal.

In the method of the first embodiment, the MRI scanner can be a 1.5T scanner or a 3.0T scanner.

In the method of the first embodiment, one or more of the one or more coronary blood vessels can be selected from the group consisting of: a left coronary artery (LCA), a right coronary artery (RCA), a circumflex artery, and a left anterior descending artery (LAD). Further, the subject can be a mammal or a human.

In a second embodiment, there is provided a method for compensating for motion-induced artifacts in magnetic resonance imaging (MRI) data. The method includes: (a) performing an MRI scan of a region of interest (ROI) comprising one or more coronary blood vessels within a subject, thereby acquiring MRI data, (b) separating the acquired imaging data into a plurality of cardiac subsets and a plurality of respiratory subsets, based upon cardiac motion and respiratory motion, (c) performing respiratory motion-corrected four dimensional (4D) reconstruction to compensate for one or more deformations between one or more respiratory phases, (d) identifying one or more quiescent cardiac phases, (e) estimating one or more non-rigid deformations between said cardiac phases, and (f) reconstructing an image comprising one or more portion of the one or more coronary blood vessels by utilizing non-rigid motion correction, thereby compensating for motion-induced artifacts in the MRI data.

In the method of the second embodiment. one or more resulting deformations due to cardiac and respiratory motion are incorporated into an L1 regularized iterative reconstruction framework. Further, a sensitivity encoding operation is performed by using a gridding/re-gridding approach.

In the method of the first embodiment, the MRI scanner can be a 1.5T scanner or a 3.0T scanner.

In the method of the first embodiment, one or more of the one or more coronary blood vessels can be selected from the group consisting of: a left coronary artery (LCA), a right coronary artery (RCA), a circumflex artery, and a left anterior descending artery (LAD). Further, the subject can be a mammal or a human.

In a third embodiment of the present invention, there is provided a magnetic resonance imaging (MRI) system. The system includes: (1) a magnet operable to provide a magnetic field, (2) a transmitter operable to transmit to a region within the magnetic field, (3) a receiver operable to receive a magnetic resonance signal from the region, and (4) a processor operable to control the transmitter and the receiver. In the system, the processor is configured to direct the transmitter and receiver to execute a sequence, which includes (a) acquiring magnetic resonance data from a coronary blood vessel within a region of interest (ROI) that comprises all or a portion of a subject's heart, according to the method of first embodiment, and (b) generating one or more images based on the magnetic resonance data acquired.

In the third embodiment, the magnetic field strength of the MRI system can be 1.5T or 3.0T.

Further, the system of the third embodiment can be configured to image one or more coronary blood vessels selected from the group consisting of: a left coronary artery (LCA), a right coronary artery (RCA), a circumflex artery, and a left anterior descending artery (LAD). Further, the subject can be a mammal or a human.

In a fourth embodiment of the present invention, a non-transitory machine-readable medium is provided, having machine executable instructions for causing one or more processors of a magnetic resonance imaging (MRI) machine to execute the imaging method of first embodiment.

BRIEF DESCRIPTION OF THE DRAWINGS

Exemplary embodiments are illustrated in the referenced figures. It is intended that the embodiments and figures disclosed herein are to be considered illustrative rather than restrictive.

FIGS. 6A, 6B, 6C, 6D, 6E, 6F, 6G, 6H, 6I, and 6J depict, in accordance with various embodiments of the invention, quantitative comparisons of image quality metrics and scan efficiency of the two reconstructions: the novel reconstruction from the extended acceptance window significantly increased aSNR compared with conventional gating with a smaller window (FIG. 6A); the extended acceptance window more than doubled the scan efficiency (FIG. 6B); the novel method significantly improved the sharpness of LM, proximal and middle RCA, and proximal LAD compared with conventional gating (FIGS. 6C-6J).

DETAILED DESCRIPTION

Figure 1:
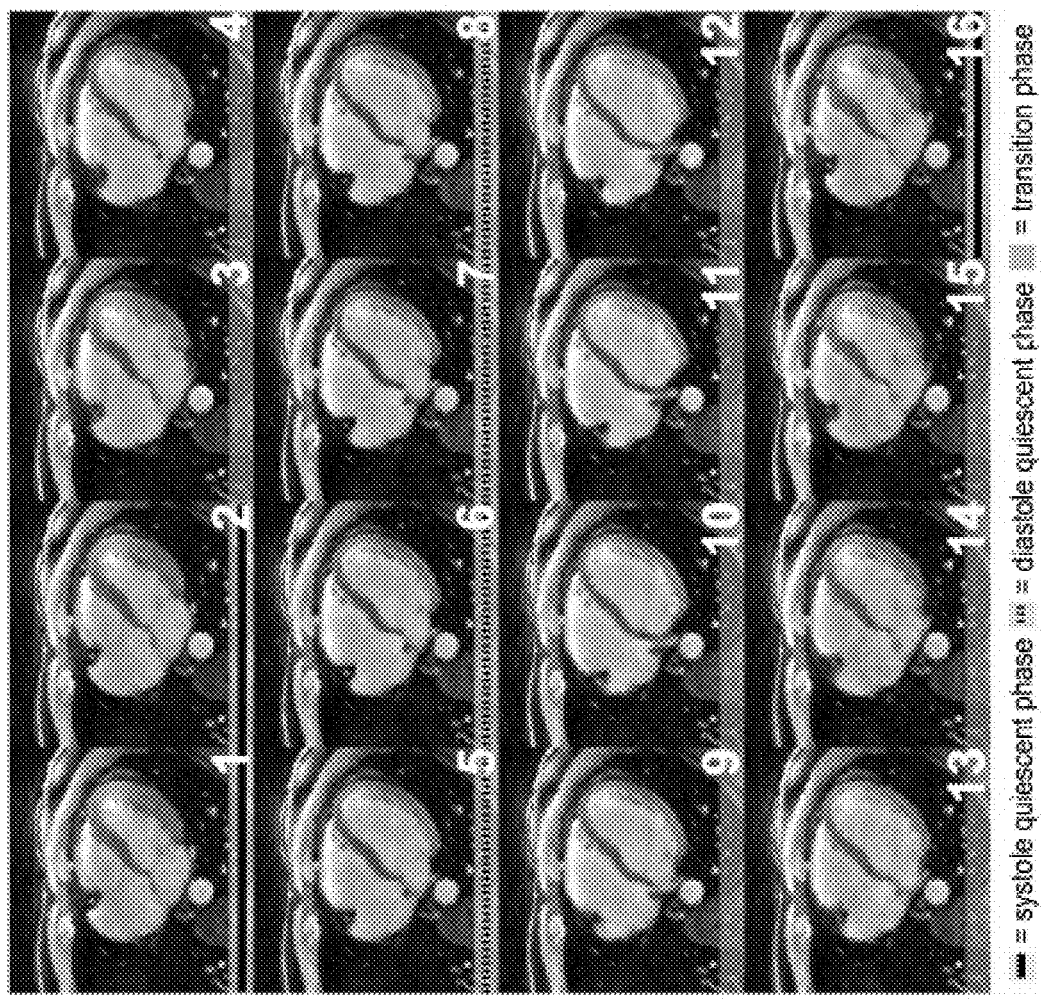
FIG. 1 depicts, in accordance with various embodiments of the invention, motion of a mid-RCA segment throughout the entire cardiac cycle reconstructed from a 4D coronary MRA acquisition: the coronary artery stayed relatively still during phases 1, 2, and 16, the systolic quiescent period, and phases 5-8, the diastolic quiescent period. All other phases exhibit significant intraphase motion as evidenced by the blurry RCA segment. The conventional gating strategy places the acceptance window within one of the quiescent periods, e.g., phases 5-8 for this subject, while discarding the data from the other phases.

All references cited herein are incorporated by reference in their entirety as though fully set forth. Unless defined otherwise, technical and scientific terms used herein have the same meaning as commonly understood by one of ordinary skill in the art to which this invention belongs. Westbrook et al., *MRI in Practice* $4^{th}$ ed., and Guyton and Hall, *Textbook of Medical Physiology* $12^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions" and "disease conditions," as used herein, may include but are in no way limited to coronary artery disease, including coronary artery disease characterized by coronary artery stenosis and plaque build-up, non-ischemic myocardial disease characterized by the functional, structural, and compositional changes in the myocardium, congenital heart disease characterized by structural and functional defects of the heart, and the like.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

In various embodiments, the present invention teaches acquiring MRI data using a 4D continuous radial acquisition scheme without the need for ECG gating or breath-holding. In some embodiments, through advanced image reconstruction techniques, the technique effectively accomplishes retrospective cardiac respiratory "self-gating" (i.e., no need for external motion surrogates such as ECG or diaphragm navigator), achieves excellent image quality with high spatiotemporal resolution, and high acquisition efficiency enabled by non-rigid motion correction (nearly 100% respiratory gating efficiency and up to 50% or morecardiac gating efficiency), which enables the total scan time to be significantly reduced to as short as 5 minutes or less.

In various embodiments, the invention teaches a method for performing magnetic resonance imaging utilizing an MRI scanner by applying a pulse sequence that consists of, consists essentially of, or comprises an ungated, spoiled gradient echo acquisition with golden-angle 3D radial trajectory. In some embodiments, water-selective excitation pulses are used to suppress fat signal. In some embodiments, the excitation pulses are slab-selective for suppressing outer volume signal. In some embodiments, the pulse sequence parameters are as follows: non-selective or slab-selective radiofrequency (RF) pulse with optional water-excitation, slab-selective excitation thickness=20-400 mm, repetition time/echo time (TR/TE)=2-10/1-5 ms, flip angle=5-90°, bandwidth=200-1200 Hz/pixel, FOV=20-400$^3$ mm$^3$, matrix size=64-512, total number of lines=5000-10000, scan time=1-10 min, contrast enhancement with a T1-shortening agent. In some embodiments, an alternative method for contrast enhancement may include, but is in no way limited to T2-weighted imaging using balanced steady-state free-precession or T2 preparation. In some embodiments, contrast enhancement is excluded. In some embodiments, the pulse sequence parameters are as follows: 1-2-1 water selective radiofrequency (RF) pulse, slab-selective excitation thickness=160 mm, repetition time/echo time (TR/TE) =6.0/3.7 ms, flip angle=15°, bandwidth=449 Hz/pixel, FOV=3203 mm3, matrix size=3203, total number of lines=99,994, scan time=10 min, contrast enhancement with a 0.20 mmol/kg Gd-BOPTA (Multi-Hance, Bracco Imaging SpA, Milano, Italy) injected at 0.3 mL/s before image acquisition.

In some embodiments, the method further includes image reconstruction. In some embodiments, cardiac and respiratory motion are resolved into different motion phases using projection-based self-gating. In some embodiments, respiratory motion is then corrected using affine transform and all respiratory phases are combined. In some embodiments, a 4D cine series is then reconstructed. In some embodiments, subsequently, cardiac motion from a subset of cardiac phases is estimated using a non-rigid motion model. In certain embodiments, a high-resolution 3D image is then reconstructed using a regularized and motion corrected iterative program, as described in greater detail herein below. In some embodiments, image reconstruction is implemented offline using MATLAB (Mathworks, Natick, Mass.) with parallel computing toolbox on a workstation. In some embodiments, the workstation includes a 12-core Intel Xeon CPU and 96 GB memory. In some embodiments, the image registration and motion correction routine is implemented using the ANTS package (http://www<dot>picsl<dot>upenn<dot>edu/ANTs). In some embodiments, the images are reformatted using OsiriX (v5.8.5 32-bit, Pixmeo, Geneva, Switzerland). In some embodiments, as described in the non-limiting detailed examples set forth herein, the general acquisition and reconstruction framework follows Pang J, et al., ECG and navigator-free four-dimensional whole-heart coronary MRA for simultaneous visualization of cardiac anatomy and function. Magn Reson Med 2014; 72:1208-1217. In some embodiments, a contrast- enhanced, spoiled gradient echo sequence with 3D radial trajectory and 1D superior-inferior (SI) self-gating (SG) is used for continuous data acquisition during free breathing. During reconstruction, the cardiac and respiratory motion signals are first extracted automatically from the multichannel SG projection time series using principal component analysis and prior knowledge of cardiac and respiratory frequencies. Then, the k-space data is assigned to a plurality of cardiac and a plurality of respiratory bins, taking advantage of the flexibility offered by the golden-means ordering in both azimuthal and polar angles (See Chan R W, et al. Temporal stability of adaptive 3D radial MRI using multidimensional golden means. Magn Reson Med 2009; 61:354-363). In certain embodiments, low-resolution images are reconstructed from each bin for affine transform based, bin-by-bin respiratory motion estimation, and the motion is subsequently corrected in k-space, individually for each cardiac phase. Although the use of nine cardiac and six respiratory bins are described in the specific examples set forth herein, a different number of cardiac and respiratory bins could be used without departing from the scope of the invention. In certain embodiments, the reference respiratory position is chosen as the one with the highest number of lines available. In certain embodiments, the reference respiratory position selected is at the end of a subject's expiration. In some embodiments, once the respiratory motion is corrected and all respiratory bins are combined, the mean cardiac cycle is resampled and a 4D image series (e.g., the 16-phase image series demonstrated in the examples) is reconstructed. In some embodiments, the 4D series is reconstructed using an iterative approach similar to Kim et al (See Kim D, et al., Accelerated phase-contrast cine MRI using k-t SPARSE-SENSE. Magn Reson Med 2012; 67:1054-1064) that combines sensitivity encoding and temporal regularization. In some embodiments, the regularization parameters are empirically determined and kept constant for all subjects.

As indicated in the specific non-limiting examples set forth herein, in some embodiments, in terms of cardiac motion correction, the cardiac phases are found in which both left and right coronary branches are relatively stationary. In some embodiments, the quiescent phases are identified solely based on the motion of the mid-RCA segment. In certain embodiments, the reference phase for cardiac motion correction is chosen as the middle of the diastolic quiescent window, or middle of the systolic window if all quiescent phases are in systole. Then, a heart mask is automatically generated using a multiatlas method and serves as the region of interest (ROI) of the registration algorithm. In some embodiments, all selected frames are also cropped to the bounding box of the heart mask to speed up the computation and reduce the memory requirement. In certain embodiments, a symmetric diffeomorphic algorithm (See Avants B B, et. al., Symmetric diffeomorphic image registration with cross-correlation: evaluating automated labeling of elderly and neurodegenerative brain. Med Image Anal 2008; 12:26-41; and Tustison N J, Avants B B. Explicit B-spline regularization in diffeomorphic image registration. Front Neuroinform 2013; 7:39) is used with cross-correlation cost function and two Laplacian-filtered versions of the original image, with different variances, as additional contrasts. In some embodiments, the estimated motion information between each moving phases and the reference, including rigid, affine, and deformable transformations, are saved for use in subsequent image reconstruction.

Figure 3:
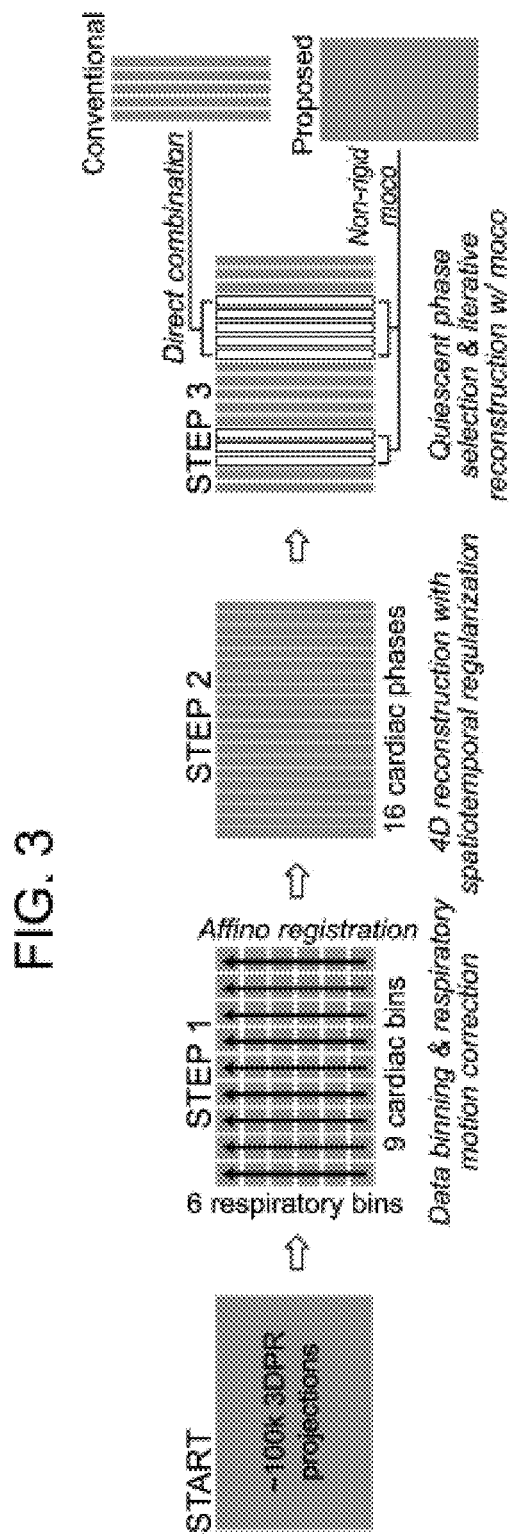
FIG. 3 depicts, in accordance with various embodiments of the invention, a reconstruction workflow: starting with the continuously acquired 3D projection reconstruction k-space data, first the dataset is segmented into multiple cardiac/respiratory phases, and the respiratory motion is corrected using affine transform separately for each cardiac phase. Then, a 16-phase cardiac cycle is reconstructed. Last, the quiescent phases are identified and combined with or without motion correction.

In some embodiments, all cardiac phases, including the systolic ones that come with large deformations, are effectively aligned with the mid-diastolic reference frame. In some embodiments, with the included phases identified and the motion information calculated, the motion-corrected reconstruction follows a previously proposed framework that iteratively inverts an encoding operator that incorporates both the sensitivity encoding operation and cardiac deformations estimated from the registration step (See Schmidt J F, et. al., Nonrigid retrospective respiratory motion correction in whole-heart coronary MRA. Magn Reson Med 2011; 66:1541-1549; Batchelor P G, et. al., Matrix description of general motion correction applied to multishot images. Magn Reson Med 2005; 54:1273-1280; Usman M, et. al., Motion corrected compressed sensing for free-breathing dynamic cardiac MRI. Magn Reson Med 2013; 70:504-516):

$$\hat{x}=\mathrm{argmin}\{|Ex-y|_2^2+\lambda|TV(x)|_1\} \qquad [1]$$

where x is the unknown image in the reference cardiac phase, E is the encoding operator that maps x to the multichannel, multicardiac phase k-space data y, TV( ) is the spatial total variation (TV) operator, and λ is the weight of the spatial TV regularization. In some embodiments, the forward operator is implemented as follows:

$$Y_{channel,phase}=FT_{phase}[S_{channel}*T_{phase}^{-1}(x)] \qquad [2]$$

where FT is the nonuniform Fourier transform that transforms between image space and the specific non-Cartesian k-space locations of a particular cardiac phase, S is the self-calibrated sensitivity map, and $T^{-1}$ is the spatial deformation from the reference to a particular cardiac phase. In some embodiments, the backward operator, which combines all included k-space data to yield an image in the reference cardiac phase, is implemented as follows:

$$x=\Sigma_{channel,phase}S_{channel}**T_{phase}[FT^{-1}(y_{channel,phase})] \qquad [3]$$

where T is the spatial transformation from a particular phase to the reference. In some embodiments, the iterative reconstruction program is implemented using a nonlinear conjugate gradient solver. In some embodiments, the entire image reconstruction workflow is as shown in FIG. 3.

In some embodiments, the invention teaches a method of magnetic resonance imaging for acquiring a four dimensional (4D) image of a region of interest (ROI) within a subject that includes one or more portions of one or more blood vessels. In some embodiments, the one or more blood vessels include one or more arteries. In some embodiments, the image includes one or more complete coronary blood vessels. In some embodiments, one or more of the arteries may include, but are in no way limited to a left coronary artery (LCA), a right coronary artery (RCA), a circumflex artery, and a left anterior descending artery (LAD). In some embodiments, the method includes the steps of (a) positioning the ROI within a subject in a magnetic field of a magnetic resonance imaging (MRI) scanner, (b) utilizing the MRI scanner to apply readout pulses (e.g., the readout pulses described above) to acquire imaging data from the ROI continuously, and (c) obtaining raw imaging data from the scanner. In some embodiments, the method further includes using a computing device to reconstruct the image from the raw imaging data. In some embodiments, the computing device is an offline workstation. In some embodiments, the ROI includes an entire heart of a subject. In some embodiments, the subject is a mammal. In some embodiments, the subject is a human. In some embodiments, the subject is a male. In some embodiments, the subject is a female. In some embodiments, the subject has arrhythmia. In some embodiments, the subject is a child. In some embodiments, the subject is an uncooperative adult or child. In some embodiments, the offline workstation is utilized in conjunction with a workstation directly associated with the MRI scanner in order to accomplish parallel processing. In some embodiments, multiple offline workstations are employed in order to further accelerate parallel processing.

In some embodiments, the invention teaches a method of signal processing to compensate for motion-induced artifacts in MR measurement data. In some embodiments, the method includes the following steps: (a) separating imaging data acquired as described above into subsets based on cardiac and respiratory motion, (b) performing respiratory motion-corrected 4D reconstruction, (c) identifying quiescent cardiac phases (e.g., by any method described or referenced herein) and estimating the non-rigid deformation between these phases (e.g., by any method described or referenced herein), and (d) reconstructing a high-quality image with non-rigid motion correction (e.g., by any method described or referenced herein). In some embodiments, the resulting deformations due to cardiac and respiratory motion are incorporated into an L1 regularized iterative reconstruction framework that utilizes sensitivity encoding. In some embodiments, the sensitivity encoding operation is performed using a gridding/regridding approach implemented using a graphics processing unit (GPU).

In various embodiments, the invention teaches a magnetic resonance imaging (MRI) system, that includes (1) a magnet operable to provide a magnetic field; (2) a transmitter operable to transmit to a region within the magnetic field; (3) a receiver operable to receive a magnetic resonance signal from the region; (4) a processor operable to control the transmitter and the receiver; and (5) a non-transitory computer-readable medium. In some embodiments, the processor is configured to direct the transmitter and receiver to execute a sequence encoded on the non-transitory computer-readable medium that includes the steps of (a) utilizing the MRI scanner to apply readout pulses to acquire imaging data from the ROI continuously, and (c) obtaining raw data from the scanner. In some embodiments, the readout pulses are any of the readout pulses described above and in the "Examples" section. In some embodiments, the system further includes a computing device suitable to reconstruct the image from the raw data according to the methods described herein. In some embodiments, the computing device is an offline workstation. In some embodiments, the ROI includes an entire heart of a subject, along with multiple coronary blood vessels associated therewith. In some embodiments, the blood vessels include one or more coronary arteries (e.g., as described above). In some embodiments, the offline workstation is utilized in conjunction with a workstation directly associated with the MRI scanner in order to accomplish parallel processing. In some embodiments, multiple offline workstations are employed in order to further accelerate parallel processing. In some embodiments, the subject is a human. In certain embodiments, the MRI system is a 1.5 T system, a 3.0 T system, a 7.0T system, but one of skill in the art would readily appreciate that an MRI system of any appropriate strength could be used.

In various embodiments, the invention teaches a non-transitory machine-readable medium having machine executable instructions for causing one or more processors of a magnetic resonance imaging (MRI) machine/scanner, and/or a subsystem configured to function therewith, to execute an imaging method, said method including: performing a method described above for imaging a blood vessel within a region of interest (ROI) that includes all or a portion of a subject's heart. In some embodiments, the blood vessel is a coronary artery. In certain embodiments, the imaging parameters are within the range of imaging parameters described herein. In some embodiments, the subject is a human.

Figure 7:
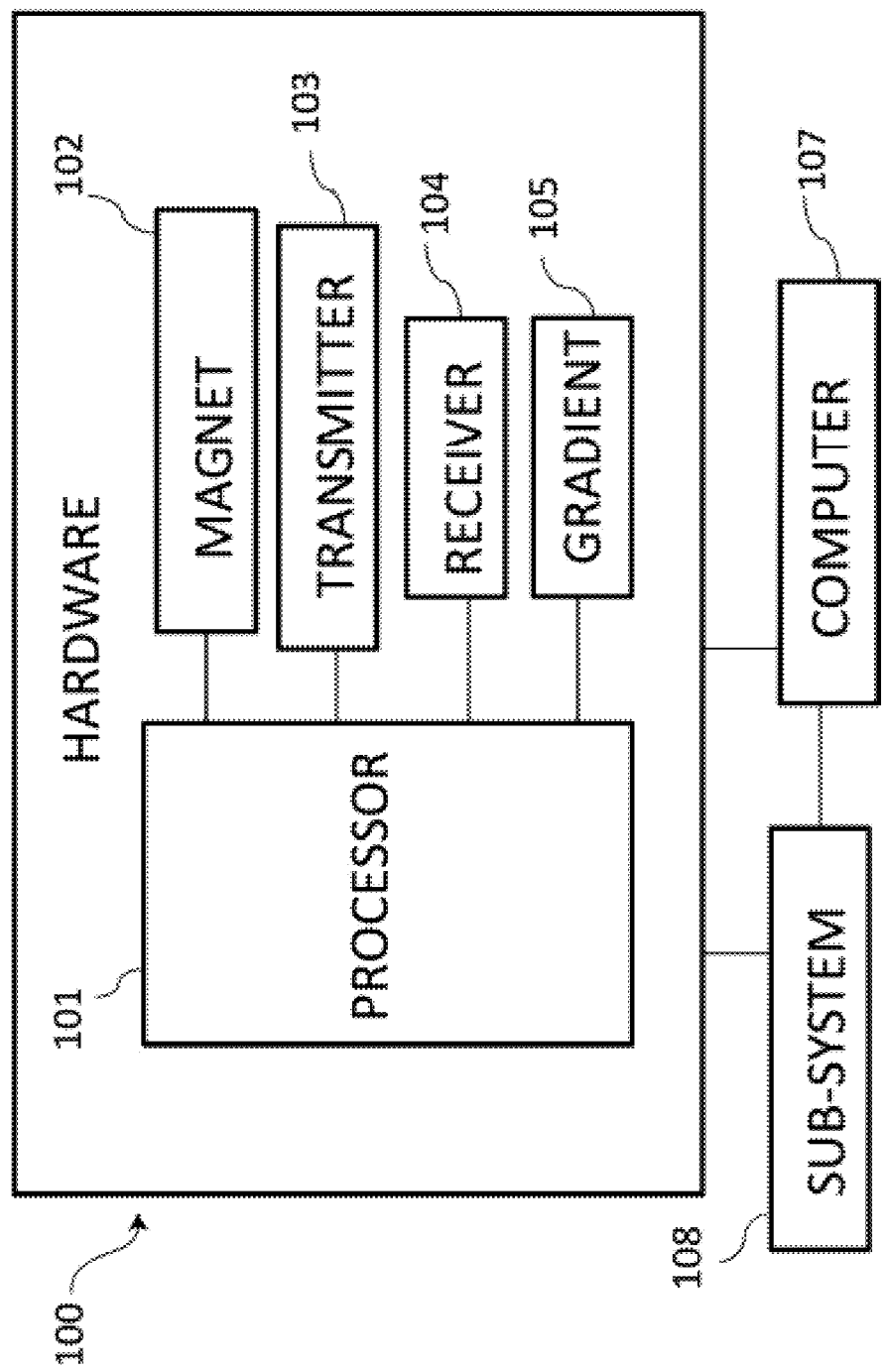
FIG. 7 depicts a system in accordance with various embodiments of the invention.

One of skill in the art would also readily appreciate that several different types of imaging systems could be used to perform the inventive methods described herein. Merely by way of example, the imaging systems described in the examples could be used. FIG. 7 also depicts a view of a system 100 that can be used to accomplish the inventive methods. System 100 includes hardware 106 and computer 107. Hardware 106 includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103 can represent a radio frequency transmitter, a power amplifier, and an antenna (or coil). Receiver 104, as denoted in the figure, can represent a receiver antenna (or coil) and an amplifier. In the example shown, transmitter 103 and receiver 104 are separately represented, however, in one example, transmitter 103 and receiver 104 can share a common coil. Hardware 106 includes gradient 105. Gradient 105 can represent one or more coils used to apply a gradient for localization.

Processor 101, in communication with various elements of hardware 106, includes one or more processors configured to implement a set of instructions corresponding to any of the methods disclosed herein. Processor 101 can be configured to implement a set of instructions (stored in memory of hardware 106 or sub-system 108) to provide RF excitation and gradients and receive magnetic resonance data from a region of interest. Sub-system 108 can include hardware and software capable of facilitating the processing of data generated by hardware 106, in conjunction with, or as a substitute for, the processing associated with image reconstruction that is normally handled by processor 101 in an MRI machine. One of skill in the art would readily appreciate that certain components of the imaging systems described herein, including the processor 101 and/or sub-system 108, are used to execute instructions embedded on a computer readable medium to implement the inventive data acquisition and image reconstruction methods described herein.

In some embodiments, computer 107 is operably coupled to hardware 106 and sub-system 108. Computer 107 can include one or more of a desktop computer, a workstation, a server, or a laptop computer. In one example, computer 107 is user-operable and includes a display, a printer, a network interface or other hardware to enable an operator to control operation of the system 100.

In some embodiments, the invention includes using any of the methods or systems described herein to diagnose a subject with the presence or absence of coronary artery disease at any stage, based upon the data and/or images acquired. In some embodiments, the coronary artery disease is characterized by stenosis. In some embodiments, the stenosis is 1-100%, 5-95%, 10-90%, 15-85%, 20-80%, 25-75%, 30-70%, 35-65%, 40-60%, or 50%. In some embodiments, the stenosis is greater than 50%. In some embodiments, the coronary artery disease is characterized by plaque build-up. In some embodiments, the plaque is unstable plaque.

In some embodiments, the invention includes treating a patient who was diagnosed with coronary artery disease according to the aforementioned methods. In some embodiments, the treatment may include administering a therapeutic amount of one or more medication that may include, but is in no way limited to, a statin, niacin, a fibrate, a bile acid sequestrant, a blood thinner, a beta blocker, nitroglycerin, an angiotensin-converting enzyme (ACE) inhibitor, an angiotensin II receptor blocker (ARB). In some embodiments, the treatment may also include, or may alternatively include a surgical intervention of a type such as, but is in no way limited to, angioplasty, stent placement, coronary artery bypass surgery.

One skilled in the art will recognize many methods and materials similar or equivalent to those described herein, which could be used in the practice of the present invention. Indeed, the present invention is in no way limited to the methods and materials described.

EXAMPLES

Example 1

By way of additional background, coronary arteries are challenging structures to image using MRI due to the small caliber, tortuous course, and continual motion. Therefore, successful coronary MR angiography (MRA) uses high-resolution, whole-heart imaging, and effective motion suppression. Current free-breathing protocols use segmented acquisitions with prospective electrocardiography (ECG) and navigator gating to suppress cardiac and respiratory motion artifacts, respectively. With data accepted only from a particular cardiac (usually mid- diastole) and respiratory (usually end-expiratory) phase, these motion suppression strategies often lead to prolonged scan time, are susceptible to variations in motion pattern, and require time-consuming setup procedures.

Several investigators have explored the potential to relax the gating constraint and perform motion correction to improve the imaging efficiency while suppressing motion artifacts.

Such strategy has been most prominently applied to addressing respiratory motion, in which all respiratory phases are accepted during acquisition, and the respiratory motion between respiratory phases are retrospectively corrected using information derived from self-navigation projections, image-based navigator through interleaved acquisitions, or respiratory phase resolved reconstruction from the imaging data. One- and multidimensional translation, affine, and nonrigid motion models have been used to correct for respiratory motion. Compared with prospective gating, these techniques significantly reduce the scan time and largely eliminate the scan time uncertainty, as the acquisition now takes a fixed number of heartbeats to complete.

Addressing the cardiac motion using an analogous approach is significantly more challenging. The coronary arteries move constantly. Variation in the velocity of such motion creates quiescent periods within the cardiac cycle, during which the coronary displacement is relatively small and the motion can be "frozen" given a sufficiently short acquisition window. There are typically two quiescent periods within a cardiac cycle, one during peak systole and another during mid-diastole. The duration and relative location of such periods vary considerably for different subjects, change with the heart rate, and differ between left and right (RCA) coronary arteries.

The conventional strategy for cardiac gating prescribes the data acceptance window such that both intra- and interphase motion are minimized, which means the window is usually well within one of the quiescent periods, and all other cardiac phases remain unused. Previous efforts on relaxing the interphase motion requirement include a 2D real-time imaging-based approach by Hardy et al with selective averaging (See Hardy C J, et. al., Coronary angiography by real-time MRI with adaptive averaging. Magn Reson Med 2000; 44: 940-946), and a volume targeted approach with extended acquisition window and affine motion correction by Stehning et al. (See Stehning C, et. al., Free breathing 3D balanced FFE coronary magnetic resonance angiography with prolonged cardiac acquisition windows and intra-RR motion correction. Magn Reson Med 2005; 53:719-723.). Due to the higher frequency (~1 Hz) and highly deformable nature of cardiac motion, successful execution of the cardiac motion correction concept benefits from high spatiotemporal resolution, whole-heart coverage, and a realistic motion model with local deformations.

The 4D whole-heart coronary MRA is a recent development that may provide the foundation for further improving the flexibility and accuracy of cardiac motion correction. The 4D approach acquires data continuously while simultaneously recording cardiac and respiratory motion information through either self-navigation alone (See Pang J, et al., ECG and navigator-free four-dimensional whole-heart coronary MRA for simultaneous visualization of cardiac anatomy and function. Magn Reson Med 2014; 72:1208-1217) or a combination of ECG and self-navigation (See Coppo S, et al., Free-running 4D wholeheart self-navigated golden angle MRI: initial results. Magn Reson Med 2015; 74:1306-1316). It completely removes the scan time uncertainty, enables the flexibility to retrospectively exclude motion outliers, and offers the ability to assess the coronary arteries and left-ventricle (LV) function from a single acquisition. During image reconstruction, the respiratory motion is corrected first, and then multiple cardiac phases are reconstructed using the cardiac trigger information derived from self-navigation or ECG. Finally, an acceptance window, within which the coronary arteries remain relatively stationary, is identified and the corresponding data are used to reconstruct a high quality image for coronary visualization. The set of cardiac phases included in such acceptance windows is always contiguous, as only one of the two typical quiescent periods, peak-systole and mid-diastole, can be included to avoid introducing artifacts from interphase cardiac motion. Usually 10-20% of the total data are accepted (See Pang J, et al., ECG and navigator-free four-dimensional whole-heart coronary MRA for simultaneous visualization of cardiac anatomy and function. Magn Reson Med 2014; 72:1208-1217).

In this experiments reported herein, the cardiac gating efficiency of 4D coronary MRA was improved by extending the cardiac acceptance window beyond a single quiescent period. First, a non-rigid registration algorithm was implemented to align all included cardiac phases to a reference phase, suppressing the interphase motion within the extended acceptance window. Then, an iterative reconstruction method was implemented that incorporated the motion information to yield a motion-free image using all data from the extended window. This method improves the achievable quality of coronary visualization from 4D coronary MRA due to the inclusion of additional data, without introducing significant cardiac motion artifacts. The method was evaluated on healthy volunteers (N=13) by comparing it with images reconstructed, without motion correction, from a conventional quiescent window, using apparent SNR and coronary sharpness as the metrics of image quality.

Methods

Data Acquisition and Cine Series Reconstruction.

The general acquisition and reconstruction framework follows Pang J, et al., ECG and navigator-free four-dimensional whole-heart coronary MRA for simultaneous visualization of cardiac anatomy and function. Magn Reson Med 2014; 72:1208-1217. A contrast-enhanced, spoiled gradient echo sequence with 3D radial trajectory and 1D superior-inferior (SI) self-gating (SG) was used for continuous data acquisition during free breathing. During reconstruction, the cardiac and respiratory motion signals were first extracted automatically from the multichannel SG projection time series using principal component analysis and prior knowledge of cardiac and respiratory frequencies. Then, the k-space data were assigned to nine cardiac and six respiratory bins, taking advantage of the flexibility offered by the golden-means ordering in both azimuthal and polar angles (See Chan R W, et al. Temporal stability of adaptive 3D radial MRI using multidimensional golden means. Magn Reson Med 2009; 61:354-363). Low-resolution images were reconstructed from each bin for affine transform based, bin-by-bin respiratory motion estimation, and the motion was subsequently corrected in k-space, individually for each cardiac phase. The reference respiratory position was chosen as the one with the highest number of lines available, usually in end-expiration (See Piccini D, et al. Is there an optimal respiratory reference position for self-navigated whole-heart coronary MR angiography J Magn Reson Imaging 2016; 43:426-433). With the respiratory motion corrected and all respiratory bins combined, the mean cardiac cycle was resampled and a 16-phase 4D image series was reconstructed. In this work, instead of the frame-by-frame non-Cartesian SENSE reconstruction used in Pang et al (See Pang J, et. al. ECG and navigator-free four-dimensional whole-heart coronary MRA for simultaneous visualization of cardiac anatomy and function. Magn Reson Med 2014; 72:1208-1217.), the 4D series was reconstructed using an iterative approach similar to Kim et al (See Kim D, et al., Accelerated phase-contrast cine MRI using k-t SPARSE-SENSE. Magn Reson Med 2012; 67:1054-1064) that combines sensitivity encoding and temporal regularization. The regularization parameters were empirically determined and kept constant for all subjects.

Cardiac Motion Correction

As a first step, the cardiac phases were found in which both left and right coronary branches were relatively stationary. Although the quiescent phases of the major coronary arteries (left anterior descending (LAD), left circumflex coronary artery (LCX), and right coronary artery (RCA)) may differ, it is known that the RCA generally exhibits higher velocity and larger displacement than the left branches. Therefore, the quiescent phases were identified solely based on the motion of the mid-RCA segment and it was assumed that the left branches would be relatively stationary if the mid-RCA were so. The reference phase for cardiac motion correction was typically chosen as the middle of the diastolic quiescent window, or middle of the systolic window if all quiescent phases are in systole. Then, a heart mask was automatically generated using a multiatlas method and served as the region of interest (ROI) of the registration algorithm. All selected frames were also cropped to the bounding box of the heart mask to speed up the computation and reduce the memory requirement. A symmetric diffeomorphic algorithm (See Avants BB, et. al., Symmetric diffeomorphic image registration with cross-correlation: evaluating automated labeling of elderly and neurodegenerative brain. Med Image Anal 2008; 12:26-41; and Tustison N J, Avants B B. Explicit B-spline regularization in diffeomorphic image registration. Front Neuroinform 2013; 7:39) was used with cross-correlation cost function and two Laplacian-filtered versions of the original image, with different variances, as additional contrasts. The estimated motion information between each moving phases and the reference, including rigid, affine, and deformable transformations, were saved for use in subsequent image reconstruction.

An example of coronary motion is presented in FIG. 1, which shows an axial slice of the 16-phase cardiac cycle reconstructed from a typical 4D acquisition. In both the systole (phases 16, 1, 2) and the diastole quiescent periods (phases 5-8), the motion of the RCA is sufficiently resolved with minimal intraphase motion. In all other phases, the RCA moves at relatively high velocities and significant intraphase motion can be observed. Within each quiescent period, the interphase cardiac motion is also relatively small, yet the shapes of the heart in systolic and diastolic phases differ significantly.

Figure 2:
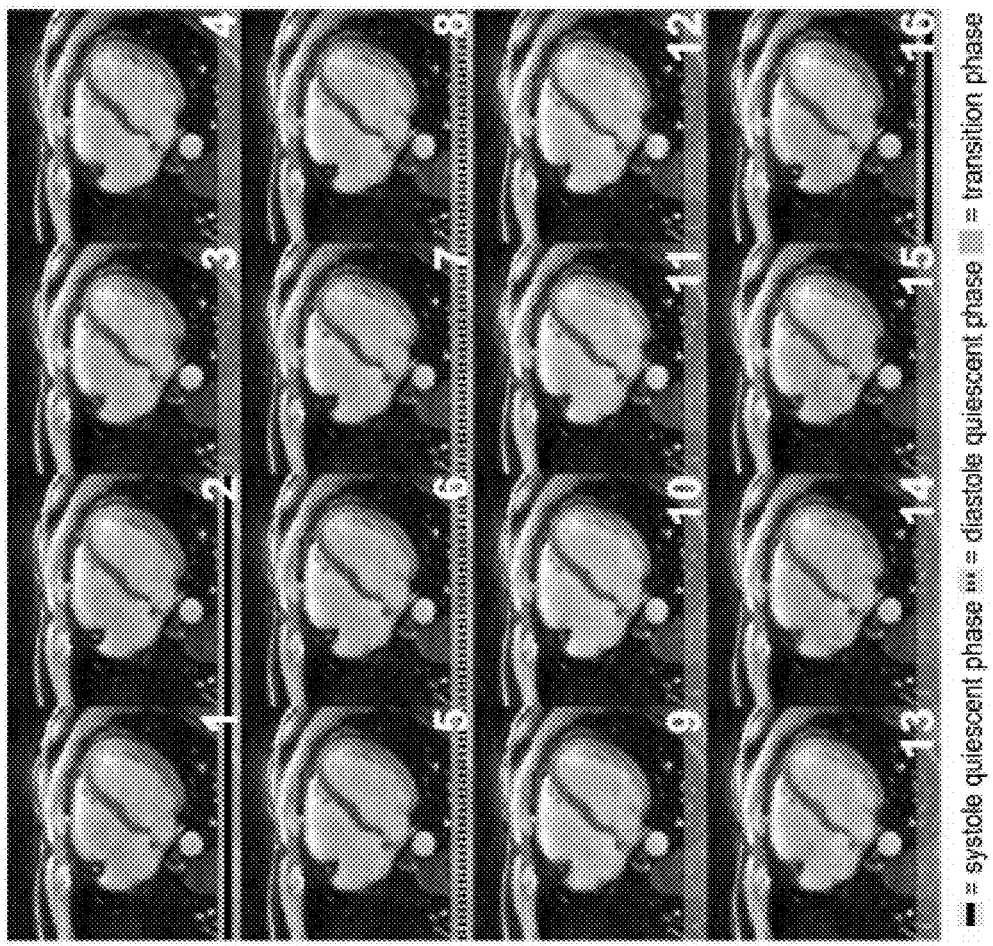
FIG. 2 depicts, in accordance with various embodiments of the invention, the cardiac cycle from the same subject in FIG. 1, after non-rigid motion correction: all phases were registered with the reference, phase 6, and may be combined without significant artifacts from interphase cardiac motion. However, the intraphase motion in phases 3, 4, 9-15, could not be corrected. Therefore, these phases would not be included in the subsequent reconstruction.

The effect of interphase cardiac motion correction is demonstrated in FIG. 2, which shows the same subject in FIG. 1 with all phases registered to phase 6. All cardiac phases, including the systolic ones that come with large deformations, are effectively aligned with the mid-diastolic reference frame. However, in the nonquiescent phases that carry significant intraphase motion, including phases 3-4 and 9-15, the RCA remain blurred despite the successful registration of the larger structures. In this example, conventional gating strategy will prescribe the acceptance window to include phases 5-8. For the inventive motion correction approach, three additional phases (1, 2, and 16) may be included, leading to a 75% increase in scanning efficiency (4/16 to 7/16).

With the included phases identified and the motion information calculated, the motion-corrected reconstruction followed a previously proposed framework that iteratively inverted an encoding operator that incorporated both the sensitivity encoding operation and cardiac deformations estimated from the registration step (See Schmidt J F, et. al., Nonrigid retrospective respiratory motion correction in whole-heart coronary MRA. Magn Reson Med 2011; 66:1541-1549; Batchelor P G, et. al., Matrix description of general motion correction applied to multishot images. Magn Reson Med 2005; 54:1273-1280; Usman M, et. al., Motion corrected compressed sensing for free-breathing dynamic cardiac MRI. Magn Reson Med 2013; 70:504-516):

$$\hat{x}=\operatorname{argmin}\{|Ex-y|_2^2+\lambda|TV(x)|_1\} \quad [1]$$

where x is the unknown image in the reference cardiac phase, E is the encoding operator that maps x to the multichannel, multicardiac phase k-space data y, TV( ) is the spatial total variation (TV) operator, and λ is the weight of the spatial TV regularization. The forward operator was implemented as follows:

$$Y_{channel,phase}=FT_{phase}[S_{channel}*T_{phase}^{-1}(x)] \quad [2]$$

where FT is the nonuniform Fourier transform that transforms between image space and the specific non-Cartesian k-space locations of a particular cardiac phase, S is the self-calibrated sensitivity map, and $T^{-1}$ is the spatial deformation from the reference to a particular cardiac phase. The backward operator, which combined all included k-space data to yield an image in the reference cardiac phase, was implemented as follows:

$$x=\Sigma_{channel,phase}S_{channel}**T_{phase}[FT^{-1}(y_{channel,phase})] \quad [3]$$

where T is the spatial transformation from a particular phase to the reference. The iterative reconstruction program was implemented using a nonlinear conjugate gradient solver. The entire image reconstruction workflow is shown in FIG. 3.

In Vivo Studies

Healthy subjects (N=13) were scanned using a clinical 3 Tesla (T) scanner (MAGNATOM Verio, Siemens Healthcare, Erlangen, Germany) with written informed consent and IRB approval. MR data was collected using a 32-channel phased coil array (Invivo Corporation, Gainesville, Fla.). The pulse sequence parameters were as follows: 1-2-1 water selective radiofrequency (RF) pulse, slab-selective excitation thickness=160 mm, repetition time/echo time (TR/TE) =6.0/3.7 ms, flip angle=15°, bandwidth=449 Hz/pixel, FOV=$320^3$ $mm^3$, matrix size=$320^3$, total number of lines=99,994, scan time=10 min, contrast enhancement with a 0.20 mmol/kg Gd-BOPTA (Multi-Hance, Bracco Imaging SpA, Milano, Italy) injected at 0.3 mL/s before image acquisition. Image reconstruction was implemented offline using MATLAB (Mathworks, Natick, Mass.) with parallel computing toolbox on a workstation with 12-core Intel Xeon CPU and 96 GB memory. The image registration and motion correction routine was implemented using the Advanced Normalization Tools (ANTs) package. The images were reformatted using OsiriX (v5.8.5 32-bit, Pixmeo, Geneva, Switzerland).

Two images were reconstructed for each subject: conventional gating without cardiac motion correction (Gating), which combined data directly from a contiguous window that exhibited minimal intra- and interphase motion, and the novel method, which accepted all phases with minimal intraphase motion and combined them with interphase cardiac motion correction (Moco). The scan efficiency, coronary sharpness, and apparent signal-to-noise ratio (aSNR) were compared using paired Student's t-test with a significance level of 0.05. The scan efficiency was defined as the ratio between the number of cardiac phases included for reconstruction and the total number of cardiac phases. The coronary sharpness was measured at left main (LM), proximal, middle, and distal segments of LADs and RCAs, and proximal LCX using the method proposed in Li D, et. al., Coronary arteries: magnetization-prepared contrast-enhanced three-dimensional volume-targeted breath-hold MR angiography. Radiology 2001; 219:270-277, which defines sharpness as the mean of the inverse distances between the 20% and 80% point on both sides of the 1D cross-section profile of a coronary segment. The aSNR was defined as the ratio between the mean signal intensity and standard deviation of a manually drawn ROI in the ascending aorta, which, considering the nonlinear and non-Cartesian reconstruction used here, was chosen as a surrogate of the true SNR.

Results

FIGS. 4A-4F show the coronal maximum-intensity projection (MIP) images from three reconstructions of two example datasets: (FIGS. 4A and 4D) conventional gating without motion correction, (FIGS. 4B and 4E) all quiescent phases combined without motion correction, and (FIGS. 4C and 4F) all quiescent phases combined with motion correction. For subject 1, the quiescent phases included ones from both systole and diastole. For subject 2, all phases were from systole, with considerable interphase motion within the extended acceptance window. For both subjects, the inventive method improved the image quality over conventional gating through including the additional data, and suppressed motion artifacts from effective motion correction. FIG. 5 shows images from five additional subjects. The respective cardiac phases used for reconstruction are also shown. Similar improvements in coronary visualization are observed.

Figure 4:
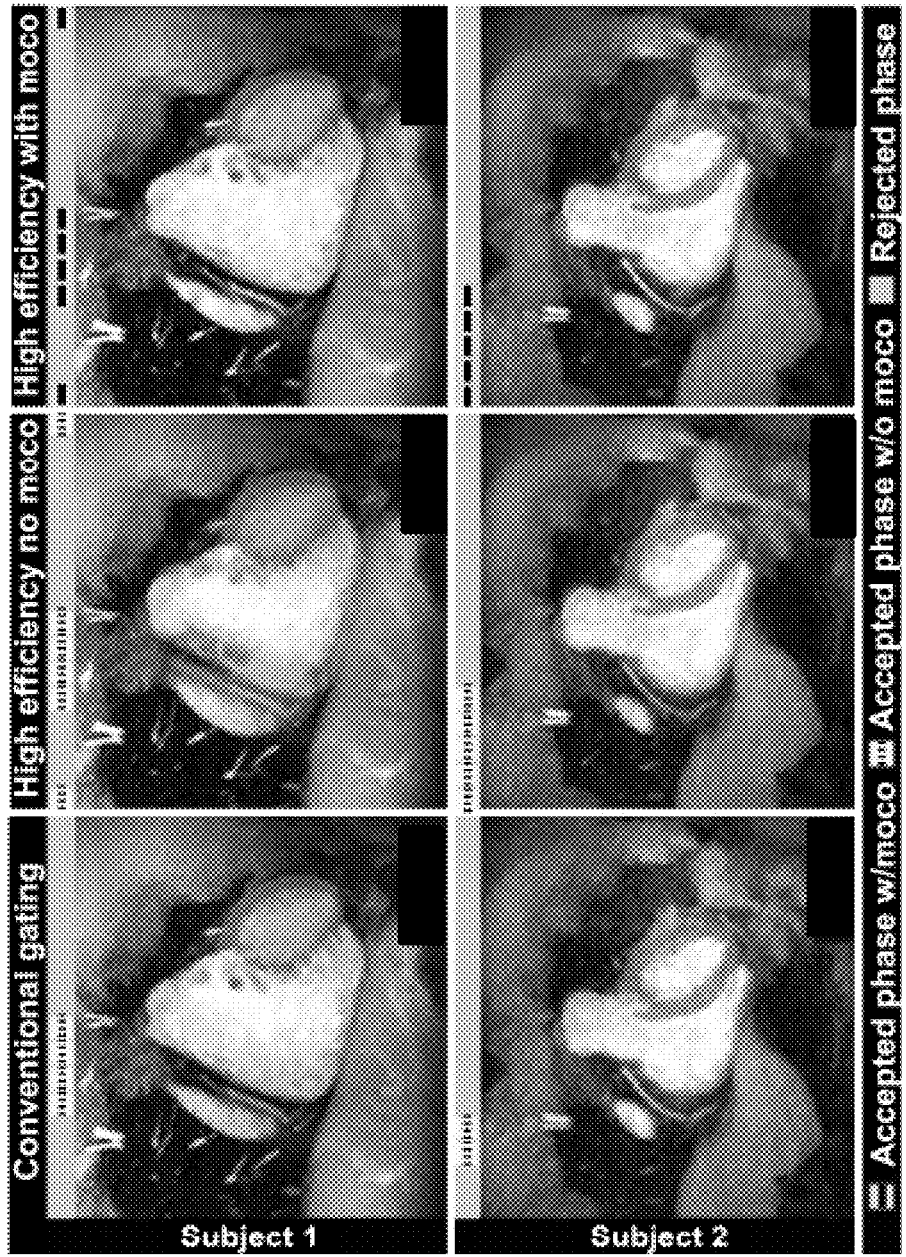
FIGS. 4A, 4B, 4C, 4D, 4E, and 4F depict, in accordance with various embodiments of the invention, coronal MIP images from three reconstructions of two example datasets: conventional gating without motion correction (FIGS. 4A and 4D); combining all quiescent phases, without motion correction (FIGS. 4B and 4E); and combining all quiescent phases, with motion correction (FIGS. 4C and 4F). For subject 1, the accepted phases included ones from both systole and diastole. For subject 2, all phases were from systole, with considerable interphase motion within the extended acceptance window. For both subjects, the novel method improved the image quality over conventional gating by making use of the additional data, while suppressing motion artifacts through effective motion correction.
Figure 5:
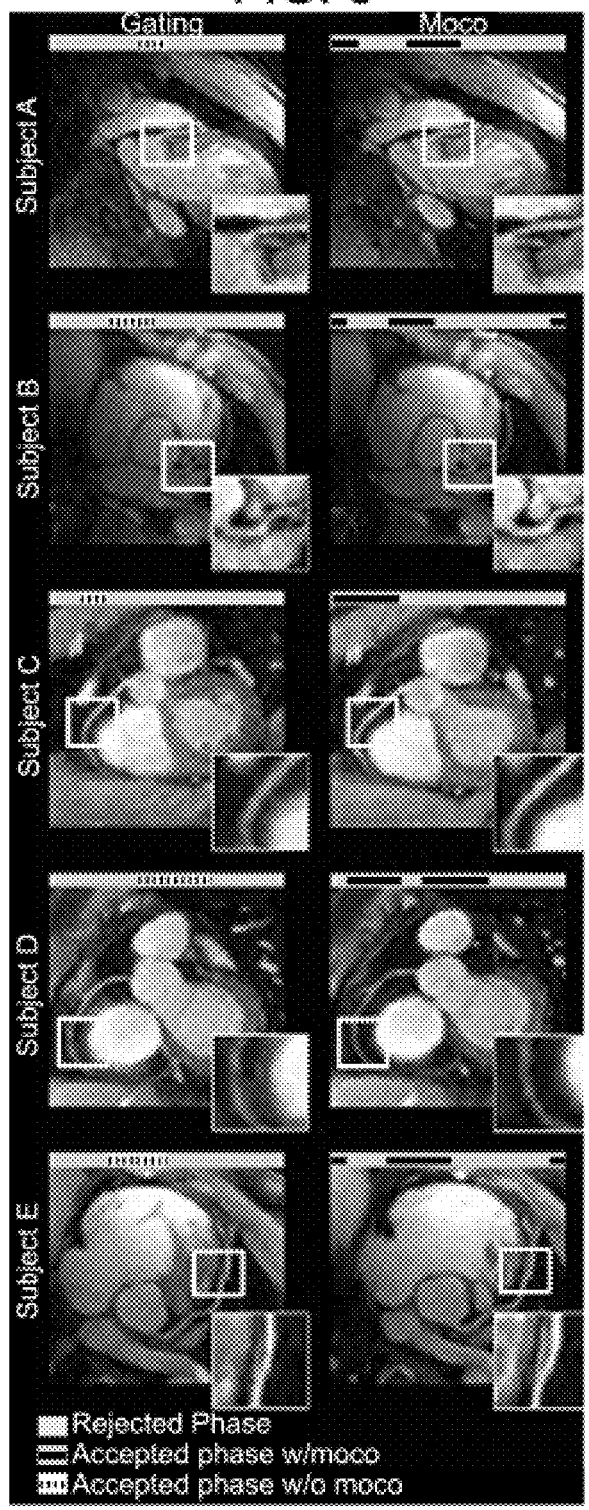
FIG. 5 depicts a system in accordance with various embodiments of the invention, five example subjects comparing conventional cardiac gating (left) with the a novel method (right). The novel method significantly improved the quality of coronary visualization.

For the majority of the subjects in this study, the extended acceptance window included phases from both systole and diastole, and direct reconstructions from such window yielded significant artifacts similar to FIG. 4B. For this reason, the quantitative analysis was not extended to such images and only Gating and Moco were compared. The mean aSNR for Gating and Moco were 11.89±3.76 and 13.97±5.21, respectively. The proposed method led to a significant improvement in aSNR (P=0.005). Moco also led to significant improvements in sharpness of LM (P=0.007), proximal RCA (P=0.04), middle RCA (P=0.02), and proximal LAD (P=0.04), over Gating. The mean scan efficiencies for Gating and Moco were 18.8%±6.0% and 40.9%±9.7%, respectively. The proposed method led to a significant improvement in scan efficiency (P<0.001). All numbers are summarized in FIGS. 6A-6J.

In this work, the quality of coronary visualization was improved from 4D coronary MRA by combining data from all quiescent phases available from the 16 reconstructed phases. Potential artifacts from interphase cardiac motion were suppressed through nonrigid motion registration and iterative reconstruction. In vivo studies on 13 healthy volunteers showed that the method significantly improved aSNR and coronary sharpness over the conventional gating strategy that only accepted data from one quiescent period.

Numerous investigations have been conducted to study the optimal placement of the cardiac acceptance window for coronary imaging. Potential quiescent periods at both systole and diastole have been identified. Gharib et al compared coronary MRA during systole and diastole, and suggested that a systolic window may be more suitable for tachycardic subjects. Uribe et al proposed to prescribe two acceptance windows in prospective ECG gating to reconstruct both systole and diastole from a single scan. Kawaji et al proposed to prescribe an extended contiguous acceptance window and retrospectively select the best subset to optimize image quality. Relatively few developments have been made to address interphase cardiac motion. Hardy et al proposed a 2D real-time imaging based technique that acquires a large number of frames and, with translation correction, selectively combines a subset where the target coronary artery appears in the imaging plane. Stehning et al proposed a prospective ECG-gated, 3D volume-targeted technique that makes use of a long (240 ms) acquisition window to reconstruct four consecutive cardiac phases, which are then motion corrected with affine transform, and averaged to yield the final reconstruction.

The experiments described herein represent major improvements over these efforts. Leveraging the whole-heart, full cardiac cycle coverage of 4D coronary MRA, the demonstrated method offers considerably more flexibility in selecting the cardiac phases (i.e., combining data from more than one contiguous periods), enables accurate characterization of the highly deformable cardiac motion in 3D, and effectively corrects such motion by means of iterative reconstruction. Compared with the original 4D coronary MRA technique, the methods of the foregoing examples offer improved coronary visualization while also allowing whole-heart LV function analysis with the 4D cine series.

The major factors that influence vessel sharpness include noise, undersampling artifacts, and motion. The first two may be alleviated from accepting more data into reconstruction, yet in the context of cardiac gating, this can only be done to a certain extent to avoid blurring from cardiac motion. With the methods of the foregoing examples, this constraint may be relaxed because now the potential blurring from interphase motion is suppressed by motion correction. Results from the study reported herein indicate that combining multiple, potentially noncontiguous phases with interphase nonrigid motion correction improves vessel sharpness over reconstructions from a smaller, contiguous set of cardiac phases. In other words, the benefit from higher SNR and lower undersampling artifacts outweighed any potential registration errors.

Due to coronary blood flow and the elasticity of the coronary wall, the size of the coronary lumen varies throughout the cardiac cycle. Previous studies using intravascular ultrasound and MRI suggested that the pulsatile variation in coronary lumen diameter is less than 5-6% for normal arteries and even less when plaque is present. Considering the size of the coronary arteries (<5 mm) and the nominal spatial resolution of the current acquisition (1.0 mm), we do not expect such variations in coronary lumen diameter to adversely affect the ability of the methods described above to perform their intended functions, i.e., detecting significant coronary stenosis (>50% reduction in diameter).

In some embodiments, there is a need to visually select the phases in which the coronary motion is sufficiently resolved (i.e., little intraphase motion), necessitating user interaction for the otherwise fully automated reconstruction routine. Automating this procedure is highly desirable and within the scope of the present invention. Several methods have been proposed in the past for automatically detecting the cardiac quiescent period from cine images, most of which are based on calculating a global interphase similarity metric throughout the cardiac cycle, and finding one or more acceptance windows by means of peak detection and thresholding (See Jahnke C, et. al., A new approach for rapid assessment of the cardiac rest period for coronary MRA. J Cardiovasc Magn Reson 2005; 7:395-399; Rasche V, et. al., Automatic extraction of the low-motion phases of the heart. In Proceedings of the 15th Annual Meeting of ISMRM, Berlin, Germany, 2007. Abstract 2545; Ustun A, et. al., Automated identification of minimal myocardial motion for improved image quality on MR angiography at 3 T. AJR Am J Roentgenol 2007; 188:W283-W290; and Huang T Y, et. al., Automatic calibration of trigger delay time for cardiac MRI. NMR Biomed 2014; 27:417-424). Alternatively, one may leverage the available 3D deformations calculated from the cardiac motion registration step, and use the similarity metrics between all deformed and the reference phase as the criterion for quiescent phases.

The promise of high imaging efficiency is two-fold. On one hand, given a fixed imaging time, more data may be included into the reconstruction, which improves SNR and reduces undersampling artifacts. On the other hand, given a fixed k-space sampling density requirement, the minimum scan time may be shortened due to the increased efficiency. In initial results, mean scan efficiency is more than doubled (18.8% to 40.9%) by incorporating additional cardiac phases, which may enable significant scan time reductions.

It is also beneficial to further reduce the temporal footprint of each reconstructed cardiac phase, which is currently around 40-60 ms (for heart rates of 60-100 bpm). Assuming an intraphase coronary displacement up to 1 mm, coronary velocities up to 17-25 mm/s may be resolved under the current temporal resolution. However, previous studies using x-ray angiography and computed tomography have reported maximum velocities of more than 100 mm/s for the RCA. Therefore, reconstructing a greater number of cardiac phases may allow a larger portion of the cardiac cycle to be accepted. Furthermore, a higher temporal resolution may also be helpful in the cases of arrhythmia, where the cardiac motion is more irregular. Another potential development is to use the motion information between motion states to improve the quality of cardiac (See Pang J, et al., ECG and navigator-free four-dimensional whole-heart coronary MRA for simultaneous visualization of cardiac anatomy and function. Magn Reson Med 2014; 72:1208-1217) or respiratory phase-resolved imaging (See Deng Z, et al., Four-dimensional MRI using three-dimensional radial sampling with respiratory self-gating to characterize temporal phase-resolved respiratory motion in the abdomen. Magn Reson Med 2016; 75:1574-1585). As the forward and inverse spatial transform between each moving and the reference phase are known, the transform between any two phases can be readily calculated. Therefore, it is possible to use the above-described framework to enhance the image quality of any individual phase by redefining the reference and the associated spatial transforms. An alternative approach is to reconstruct all phases jointly with temporal similarity constraint imposed on the motion corrected cardiac cycle (See Lingala S G, et. al., Deformation corrected compressed sensing (DC-CS): a novel framework for accelerated dynamic MRI. IEEE Trans Med Imaging 2015; 34:72-85; and Royuela-Del-Val J, et al., Nonrigid groupwise registration for motion estimation and compensation in compressed sensing reconstruction of breath-hold cardiac cine MRI. Magn Reson Med 2016; 75:1525-1536).

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law.

Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for compensating for motion-induced artifacts in magnetic resonance imaging (MRI) data, the method comprising:
    performing an MRI scan of a region of interest (ROI) comprising one or more coronary blood vessels within a subject, thereby acquiring MRI data;
    separating the acquired imaging data into a plurality of bins based upon cardiac motion and respiratory motion, each of the plurality of bins including data from one of a plurality of respiratory phases and one of a plurality of cardiac phases, such that the data for each of the plurality of cardiac phases includes data for all of the plurality of respiratory phases;
    for each cardiac phase, performing respiratory motion-corrected reconstruction to compensate for one or more respiratory deformations across all of the plurality of respiratory phases to generate respiratory motion-corrected imaging data;
    for each cardiac phase, combining the respiratory motion-corrected imaging data for all of the plurality of respiratory phases;
    identifying, from the respiratory motion-corrected imaging data, a plurality of quiescent cardiac phases and one or more non-quiescent cardiac phases;
    estimating one or more non-rigid cardiac deformations between the plurality of cardiac phases;
    identifying one of the plurality of cardiac phases as a reference cardiac phase; and
    reconstructing an image comprising one or more portions of the one or more coronary blood vessels by aligning a remainder of the plurality of quiescent cardiac phases with the reference cardiac phase utilizing non-rigid motion correction, thereby compensating for motion-induced artifacts in the MRI data from at least the one or more non-rigid cardiac deformations,
    wherein the plurality of quiescent cardiac phases includes at least a first quiescent cardiac phase and a second quiescent cardiac phase temporally separated by at least one of the one or more non-quiescent cardiac phases.

2. The method of claim 1, wherein the first quiescent cardiac phase is a systolic quiescent cardiac phase, and the second quiescent cardiac phase is a diastolic cardiac quiescent phase.

3. The method of claim 1, wherein the reference cardiac phase is one of the plurality of quiescent cardiac phases.

4. The method of claim 1, wherein the image is reconstructed using an L1 regularized iterative reconstruction framework that corrects for the one or more respiratory deformations due to respiratory motion and the one or more non-rigid cardiac deformations due to cardiac motion.

5. The method of claim 4, wherein the L1 regularized iterative reconstruction framework includes a sensitivity encoding operation that is performed by using a gridding/re-gridding approach.

6. The method of claim 1, wherein the MRI scan is performed using an MRI system with a magnetic field strength of 1.5T or 3.0T.

7. The method of claim 1, wherein one or more of the one or more coronary blood vessels are selected from the group consisting of: a left coronary artery (LCA), a right coronary artery (RCA), a circumflex artery, a left anterior descending artery (LAD), and combinations thereof.

8. The method of claim 1, wherein the subject is a mammal.

9. The method of claim 1, wherein the subject is a human.

10. A non-transitory machine-readable medium having machine executable instructions for causing one or more processors of a magnetic resonance imaging (MRI) machine to execute the imaging method of claim 1.

11. A magnetic resonance imaging (MRI) system, comprising:
- a magnet operable to provide a magnetic field;
- a transmitter operable to transmit to a region within the magnetic field;
- a receiver operable to receive a magnetic resonance signal from the region; and
- a processor operable to control the transmitter and the receiver; wherein the processor is configured to direct the transmitter and receiver to perform an MRI scan of a region of interest (ROI) comprising one or more coronary blood vessels within a subject, thereby acquiring MRI data;
- wherein the processor is further operable to:
    - separate the acquired imaging data into a plurality of bins based upon cardiac motion and respiratory motion, each of the plurality of bins including data from one of a plurality of respiratory phases and one of a plurality of cardiac phases, such that the data for each of the plurality of cardiac phases includes data for all of the plurality of respiratory phases;
    - for each cardiac phase, perform respiratory motion-corrected reconstruction to compensate for one or more respiratory deformations across all of the plurality of respiratory phases to generate respiratory motion-corrected imaging data;
    - for each cardiac phase, combine the respiratory motion-corrected imaging data for all of the plurality of respiratory phases;
    - identify, from the respiratory motion-corrected imaging data, a plurality of quiescent cardiac phases and one or more non-quiescent cardiac phases;
    - estimate one or more non-rigid cardiac deformations between the plurality of cardiac phases;
    - identify one of the plurality of cardiac phases as a reference cardiac phase; and
    - reconstruct an image comprising one or more portion of the one or more coronary blood vessels by aligning a remainder of the plurality of quiescent cardiac phases with the reference cardiac phase utilizing non-rigid motion correction, thereby compensating for motion-induced artifacts in the MRI data from at least the one or more non-rigid cardiac deformations,
- wherein the plurality of quiescent cardiac phases includes at least a first quiescent cardiac phase and a second quiescent cardiac phase temporally separated by at least one of the one or more non-quiescent cardiac phases.

12. The MRI system of claim 11, wherein the first quiescent cardiac phase is a systolic quiescent cardiac phase, and the second quiescent cardiac phase is a diastolic cardiac quiescent phase.

13. The MRI system of claim 11, wherein the reference cardiac phase is one of the plurality of quiescent cardiac phases.

14. The MRI system of claim 11, wherein the processor is operable to reconstruct the image using an L1 regularized iterative reconstruction framework that corrects for the one or more-respiratory deformations due to respiratory motion and the one or more non-rigid cardiac deformations due to cardiac motion.

15. The MRI system of claim 14, wherein the L1 regularized iterative reconstruction framework includes a sensitivity encoding operation that is performed by using a gridding/re-gridding approach.

16. The MRI system of claim 11, wherein a magnetic field strength of the magnet of the MRI system is 1.5T or 3.0T.

17. The MRI system of claim 11, wherein the image that the processor is operable to reconstruct comprises one or more portions of a left coronary artery (LCA), a right coronary artery (RCA), a circumflex artery, a left anterior descending artery (LAD), or combinations thereof.

18. The MRI system of claim 11, wherein the processor is operable to direct the transmitter and receiver to perform the MRI scan on a mammal.

19. The MRI system of claim 11, wherein the processor is operable to direct the transmitter and receiver to perform the MRI scan on a human.

* * * * *